United States Patent [19]

Murugan et al.

[11] Patent Number: 5,541,331

[45] Date of Patent: Jul. 30, 1996

[54] PROCESSES FOR PRODUCING α-PYRIDYL CARBINOLS

[75] Inventors: Ramiah Murugan, Indianapolis; Gerald L. Goe; Eric F. V. Scriven, both of Greenwood, all of Ind.

[73] Assignee: Reilly Industries, Inc., Indianapolis, Ind.

[21] Appl. No.: 482,965

[22] Filed: Jun. 15, 1995

Related U.S. Application Data

[63] Continuation of Ser. No. 153,484, Nov. 16, 1993, abandoned, which is a continuation of Ser. No. 875,747, Apr. 29, 1992, abandoned, which is a continuation-in-part of Ser. No. 693,687, Apr. 30, 1991, abandoned.

[51] Int. Cl.$^6$ .................. C07D 213/28; C07D 211/22
[52] U.S. Cl. ................. 546/343; 546/194; 546/241
[58] Field of Search .................. 546/343, 194, 546/241

[56] References Cited

U.S. PATENT DOCUMENTS 3,878,217  4/1975  Carr et al. .................. 546/191
4,835,164  5/1989  Shanklin et al. .................. 514/317

FOREIGN PATENT DOCUMENTS 1046897A  11/1990  China .................. 546/343

OTHER PUBLICATIONS

Chemical Abstracts, vol. 115 (7) Abst. No. 115:71,411p Aug. 19, 1991.

*Primary Examiner*—Alan L. Rotman
*Attorney, Agent, or Firm*—Woodard, Emhardt, Naughton, Moriarty & McNett

[57] ABSTRACT

Disclosed are preferred processes for producing α-2-pyridylα-aryl carbinol or α-4-pyridyl α-aryl carbinol compounds.

28 Claims, No Drawings

PROCESSES FOR PRODUCING α-PYRIDYL CARBINOLS

RELATED APPLICATIONS

This application is a continuation of application Ser. No. 08/153,484, filed Nov. 16, 1993, now abandoned, which is a continuation of application Ser. No. 07/875,747, filed Apr. 29, 1992, now abandoned, which is a continuation-in-part of U.S. patent application Ser. No. 07/693,687 filed Apr. 30, 1991, now abandoned.

BACKGROUND OF THE INVENTION

The present invention relates generally to processes for producing α-pyridyl carbinol compounds. More particularly, it relates to a process for producing an α-2-pyridyl α-aryl carbinol or α-4-pyridyl α-aryl carbinol by reacting a 2- or 4-cyanopyridine with an aromatic carbonyl compound.

α-Pyridyl carbonol compounds, having the characteristic Py-C-OH grouping, where Py is a pyridyl group, have been widely studied and used in large quantities as intermediates in the production of antihistamines, for instance carbinoxamine, dioxylamine, Azacyclonol and the antihistamine terferadine (Seldane®). To date, several processes for producing these α-pyridyl carbinols have received substantial interest. For example, the "Emmert reaction" involves a reaction of pyridine and ketones in the presence of a magnesium or aluminum amalgam. The reaction product includes a mixture of 2- and 4-puridyl carbinols together with pinacols formed as byproducts. See, e.g. B. Emmert and E. Asendorf, Ber., 72, 1188 (1939); B. Emmert and E. Pirot, Ber., 74, 714 (1941); and C. H. Tilford, R. S. Shelton and M. G. Van Campen, Jr., *J. Am. Chem. Soc.*, 70, 4001 (1948).

In the "Hammick reaction", α-pyridyl carbinols are produced by decarboxylation of picolinic acid in the an excess of aldehyde or ketone. See, e.g. P. Dyson and D. L. Hammick, *J. Chem. Soc.*, 1724 (1937); and K. Mislow, *J. Am. Chem. Soc.*, 69, 2559 (1947).

α-Pyridyl carbinols can also be prepared either by the action of pyridyl Grignard reagents on aldehydes or ketones, see, e.g., J. P. Wibuat and L. G. Heeringa, *Recueil*, 74, 1003 (1955), N. Furukawa, T. Shibutani, K. Matsumura, H. Fujihara, and S. Oae, *Tetrahedro Lett.*, 27, 3899 (1966), or by the action of aryl Grignard reagents on pyridyl aldehydes, ketones or esters, see, e.g., A. E. Tshitschibabin and S. W. Benewolenskaja, Ber., 61, 547 (1928); Y. Kasuya and K. Fujie, *Yakugaku Zasshi.*, 78, 551 (1958) [Chem. Abstr., 52, 17196i (1958)]; and K. Nagarjan, P. K. Talwalker, R. H. Shah and S. J. Shenoy, *Indian J. Chem.*, Sect. B, 24B, 112 (1985).

The diphenyl ketyl radical has been reported to undergo substitution reactions with cyano-substituted puridinium ions to form α-pyridinium substituted carbinols. B. M. Vittimberga, F. Minisci and S. Morrocchi, *J. Am. Chem. Soc.*, 97, 4397 (1975), reports such interactions in 1M sulfuric acid where the diphenyl ketyl radical was photochemically generated. In later work, P. McDevitt and B. M. Vittimberga, *J. Heterocyclic Chem.*, 27, 1903 (1990), such interactions are described where the diphenyl ketyl radical was generated via thermal homolysis of benzopinacol. Interactions between thermally generated diphenyl ketyl radical and cyano-substituted pyridines in neutral media were also described in this later work.

Diaryl heterocyclic carbinols have been prepared by oxidation of corresponding methylpyridines with sodium hydroxide and $O_2$ in DMOS. See, T. J. Kress and L. L. Moore, *J. Heterocyclic Chem.*, 9, 1161 (1972).

As the above and other literature demostrates, the interest in discovering highly effective and economically attractive processes for producing α-pyridyl carbinols has been and remains substantial. However, routes heretofore studied present many disadvantages. For instance, the Emmert reaction gives mixtures of 2- and 4-pyridyl carbinols and it is thus not possible to achieve highly selective production of either. The Hammick reaction requires harsh conditions and gives low yields especially when working at the 4-position of the pyridine ring (e.g. with isonicotinic acid). The difficultly in handling organmetallics together with the use of halopyridines as starting materials makes the use of Grignard reagents unattractive from economic and other standpoints. Further, low yields and significant byproduct formation commonly encountered in the above-noted work with the diphenyl ketyl radical, and the expense of the corresponding methane starting materials in the above-noted work by Kress et al. make these routes relatively disadvantageous.

What is therefore needed is a process for producing α-pyridyl carbinols which employs relatively inexpensive starting materials and can be conducted under moderate conditions. Further, more preferred routes would provide high yields and minimal byproduct formation.

SUMMARY OF THE INVENTION

The present invention addresses these and other need and provides in one preferred embodiment a process for producing an α-2-pyridyl α-aryl carbinol or an α-4-pyridyl α-aryl carbinol compound. This is achieved by reacting a 2- or 4-cyanopyridine with an α-aryl ketone or α-aryl aldehyde in the presence of a metal or metal ion electron donor and recovering therefrom the α-2-pyridyl α-aryl carbinol or α-4-pyridyl α-aryl carbinol compound.

Another preferred embodiment of the invention provides a process for producing an α-2-pyridyl α-aryl carbinol or an α-4-pyridyl α-aryl carbinol compound which includes heating and reacting a 2- or 4-cyanopyridine with an α-aryl ketone or α-aryl aldehyde in the presence of a metal or metal ion electron donor in an aromatic solvent, and recovering therefrom the α-2-pyridyl α-aryl carbinol or α-4-pyridyl α-aryl carbinol compound.

In another aspect of the invention, highly advantageous processes have been discovered in which the order of reactant addition is controlled to achieve superior product yields and minimize byproduct formation. Thus, another preferred embodiment provides a process for producing an α-2-pyridyl α-aryl carbinol or an α-4-pyridyl α-aryl carbinol compound. This preferred embodiment is characterized by initially reacting an α-aryl aldehyde or ketone in the presence of a metal or metal ion electron donor. The product of this initial reaction is subsequently reacted with a 2- or 4-cyanopyridine, and the α-aryl puridyl carbinol compound is then recovered. The initial reacting (i.e. the reaction of electron donor and aldehyde or ketone prior to the addition of the 2- or 4-cyanopyridine) can involve some or all of the total amount of the aldehyde or ketone to be reacted. For instance, in one feature aspect, the invention provides a process in which electron donor is initially reacted with the aldehyde or ketone and then the 2- or 4-cyanopyridine and further amounts of the aldehyde or ketone are added. Processes of this embodiment have demonstrated superior yields while providing good selectivity and can be conducted using a variety of conditions.

Another preferred embodiment of the invention provides a process for preparing an α-aryl pyridyl carbinol compound, comprising reacting an α-aryl ketone or aldehyde with a 2- or 4-cyanopyridine in the presence of a metal or metal ion electron donor selected from the group consisting of Group IB, IIA, IIB, IIIA, IIIB, IVA, IVB, VB, VIB and VIIB metals and ions thereof. The α-aryl pyridyl carbinol compound is then recovered.

Another preferred embodiments of the invention provides a process for preparing an α-aryl piperidyl carbinol compound form a corresponding α-aryl pyridyl carbinol compound, comprising hydrogenating the α-aryl pyridyl carbinol compound in a benzene or alkylbenzene solvent in the presence of a palladium catalyst to produce the α-aryl piperidyl carbinol compound.

The preferred embodiments of the invention employ relatively inexpensive and readily accessible starting materials, and can be conducted under moderate conditions. Further, preferred processes of the invention provide highly selective production of either 2- or 4-pyridyl carbinols in good yield and with very little byproduct formation. Additional objects and advantages of the invention will be apparent from the following description and appended claims.

DESCRIPTION OF THE PREFERRED EMBODIMENTS

For the purpose of promoting and understanding of the principles of the invention, reference will now be made to the certain embodiments and specific language will be used to describe the same. It will nevertheless by understood that no limitation of the scope of the invention is thereby intended, such alterations, further modifications and applications of the principles of the invention being contemplated as would normally occur to one skilled in the art to which the invention pertains.

As indicated above, preferred embodiments of the invention involve reaction of a 2- or 4-cyanopyridine with an α-aryl ketone or aldehyde. The cyanopyridine employed in the preferred embodiments can lack further substituents attached to its pyridine ring, or of course can include other substituents attached to the ring which do not interfere with the reaction of the cyanopyridine and the aldehyde or ketone (sometimes together hereinafter referred to as "the carbonyl compound") to give the desire product. Such non-interfering substituents can include, for example, alkyl groups such as methyl, ethyl, propyl, etc, fused aryl (e.g. naphthyl) groups and others.

As indicated, the cyanopyridine is reacted with an α-aryl ketone or aldehyde, e.g. a compound according to the formula Ar—CO—$R_1$ wherein Ar is aryl and $R_1$ is hydrogen (i.e. aldehydes); or an organic group such as branched or unbranched alkyl (preferably about $C_1$–$C_{10}$ alkyl, e.g. methyl, ethyl, propyl, butyl, etc.) alkenyl (e.g. a branched or unbranched carbon chain group, preferably about $C_1$–$C_{10}$, having one or more ethylenic unsaturations), aryl, alkaryl (e.g. -alkenyl-aryl with $C_1$–$C_{10}$ alkylene groups being preferred), alkenylaryl (e.g. -alkenyl-aryl with $C_1$–$C_{10}$ alkenyl groups being preferred) (i.e. ketones). Additionally, within this formula, —CO—$R_1$ can form an alicyclic group fused to Ar, e.g. preferably forming a fused 4, 5 or 6 membered hydrocarbon ring, which may also be fused to another aryl group, e.g. as occurs in preferred reactants such as fluorenone. Accordingly, preferred α-aryl carbonyl reactants to data have included ketones such as benzophenone, Michler's ketone (4,4'-bis(dimethylamino)benzophenone), 4,4'-difluorobenzophenone, 4-methoxybenzophenone, fluorenone and chalcone, and aldehydes such as benzaldehyde. α-Aryl ketones which are free from enolizable hydrogens (i.e. $R_1$ has no enolizable hydrogens on a carbon bonded immediately to the carbonyl group "—CO—") are preferred, for instance as provided in α,α-diaryl ketones, e.g. benzophenone. In this regard, as used herein, the term "aryl" is meant to include an aromatic cyclic or polycyclic group containing one or more unsaturated six-membered carbon-containing rings, which rings can include one or more heteroatoms such as nitrogen, oxygen or sulfur, e.g. pyridyl groups. As such, preferred aryl groups include for instance phenyl groups and groups having two or more fused benzene rings, typically two or three fused benzene rings, e.g. naphthyl, phenanthrenyl, anthracenyl, etc. Further, the aryl group can be substituted with non-interfering substitutents, for example amino groups such as alkylamino, e.g. dimethylamino, amido groups, e.g. —$NHCOCH_3$, alkoxy groups, e.g. methoxy and ethoxy, alkylsilyl groups, e.g. trimethylsilyl, or other carboxyl derivatives, e.g. —COO-alkyl or —COO-aryl, halogens, e.g. chlorine, bromine, fluorine, etc.

The term α-aryl ketone or aldehyde, then, is meant to include aldehydes and ketones in which an aryl group is immediately adjacent and bonded to a carbonyl group. Thus, the term α,α-diaryl ketones includes having two such aryl groups bonded and immediately adjacent to a carbonyl group.

The above-described α-aryl aldehyde or ketone is reacted with a 2-or 4-cyanopyridine and the product thereof (a corresponding carbinol salt precursor) is hydrolyzed so as to form an α-(2 or 4)-pyridyl α-aryl compound of the formula

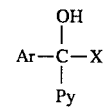

wherein Ar is as defined above Py, is a 2- or 4-pyridyl group, and X can be the same as $R_1$, or can be a group resulting from an aldol condensation and subsequent dehydration of two of the α-aryl carbonyl compound reactants, e.g. where an α-aryl ketone reactant contains an enolizable hydrogen. As an example where X will be the same as $R_1$, where $R_1$ is free of enolizable hydrogens, a reactant of the formula Ar—CO—$R_1$ reacts with the 2- or 4-cyanopyridine to form (after hydrolysis, e.g. workup with water, etc.) a respective α-2-pyridyl α-aryl carbinol or α-4-pyridyl α-aryl carbinol compound of the formula

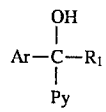

wherein Ar, Py and $R_1$ are as defined above.

One other other hand, where $R_1$ of a reactant α-aryl ketone compound has an enolizable hydrogen alpha to the carbonyl group, e.g. $R_1$=—$CH_2$—$R_2$ wherein $R_2$ can be hydrogen, alkyl, alkenyl, aryl, alkaryl, alkenylaryl, etc., X can be a group resulting from an aldol condensation and dehydration of two of the reactant α-aryl ketones. That is, two reactant molecules Ar—CO—$CH_2$—$R_2$ can undergo aldol condensation and subsequent dehydration to give an α-aryl ketone having the formula

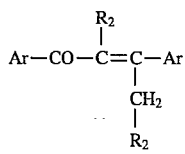

This α-aryl ketone compound can then react in situ with a 2- or 4-cyanopyridine to form (after workup) a respective α-2-pyridyl α-aryl carbinol or α-4-pyridyl α-aryl carbinol compound of the formula

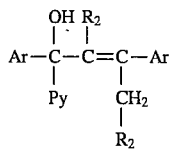

wherein Py, $R_2$ and Ar are as defined above.

It will be understood that where a ketone reactant contains an enolizable hydrogen, a mixture of carbinol products may be obtained in which $X = -CH_2-R_2$ (i.e. $X=R_1$) in some instances and X=a group resulting from an aldol condensation in other instances, with the extent of condensation of the reactants and thus distribution of such products depending upon many factors such as the particular reactant, solvent, electron donor, temperature, etc. employed in the reaction. In any event, whether or not $R_1$ contains an enolizable hydrogen, the reaction of an α-aryl ketone or aldehyde with a 2- or 4-cyanopyridine in accordance with the invention, after work up by hydrolysis, will provide an α-(2 or 4)-pyridyl α-aryl carbinol product.

As indicated, the cyanopyridine and the aldehyde or ketone are reacted in the presence of a metal or metal ion electron donor. Suitable such donors include metals or metal ions having oxidation potentials sufficiently height to cause the reaction to proceed. For example, the metal or metal ion may be selected from Group IA (e.g. alkali metals such as sodium, lithium and potassium metals), Group IB (e.g. copper metal), Group IIA (e.g. alkaline earth metals such as calcium and magnesium metals), Group IIB (e.g. zinc metal), Group IIIA (e.g. aluminum metal), Group IIIB (e.g. samarium ($Sm^{2+}$), Group IVA (e.g. tin metal), Group IVB (e.g. titanium ($Ti^{2+}$)), Group VB (e.g. vanadium metal), Group VIB (e.g. chromium metal) or Group VIIB (e.g. manganese metal). Preferably, the electron donor will have an oxidation potential of about 2.7 or above. Group IA or IIA metals such as sodium, lithium, and calcium, especially sodium, have been preferred electron donors in work to data.

The preferred process can be conducted in a wide range of solvents in which the reactants are soluble, including, for example, solvents ranging from xylene to liquid ammonia. Toluene has also proven a suitable solvent to data, and others, for instance, diglyme, protic solvents with acid, and the like will also be suitable as those skilled in the art will recognize and appreciate. As mentioned above, highly advantageous processes can be conducted in aromatic solvents.

Similarly, the reaction can be conducted over a wide range of temperatures, for instance temperatures of about −80° C. to about 200° C. will be suitable. More preferred reactions conducted to data have occurred in aromatic solvents upon heating, desirably at a temperature of at least 80° C., even more preferably in refluxing aromatic solvent, for example in refluxing aromatic hydrocarbons such as benzenes or alkylbenzenes, e.g. xylene (e.g. at about 135° C. to 145° C.), and toluene (e.g. at about 110° C.). Favorable reactions have also been conducted in liquid ammonia without heating at temperatures of about minus 33° C.

Of course, when using sodium or other similar metals are electron donor, the reaction is preferably conducted under a dry inert atmosphere for safety reasons. For example, the reaction can be conducted under a nitrogen atmosphere where appropriate.

The product can be isolated and recovered using conventional techniques, e.g. when necessary corresponding salts of the carbinols (i.e. $M^+ \text{-}OCArPyX$ where $M^+$ is a cation such as a metal ion provided by the electron donor, and Ar, Py and X are as defined above) can be worked up with water to form the carbinol product. Of course, hydrolysis will not be necessary under conditions providing direct formation of carbinols, for example when acid, protic or aqueous conditions are employed in the reaction step. Once formed, the carbinol product can then be filtered and washed with water and acetone and/or other suitable materials.

In another preferred aspect, it has been discovered that improved yields are obtained when the order and timing of addition of reactants are controlled. In particular, where adding reactants to the solvent already at reaction temperature, highly improved yields are obtained when the cyanopyridine is added after the ketone or aldehyde and electron donor. Thus, most preferred from work thus far is to combine and initially react the electron donor and ketone or aldehyde in the solvent, and thereafter add the 2- or 4-cyanopyridine. The initial reacting without the cyanopyridine is preferably continued for at least about 15 minutes, more preferably at least about 30 minutes, and most preferably about 30 to 60 minutes. The cyanopyridine can the be added and reacting (e.g. under reflux) continued, advantageously for at least about another two hours, more preferably at least about three hours. The initial reacting can include some or all of the total amount of aldehyde or ketone and electron donor to be reacted. For example, in some processes, all of the aldehyde or ketone has been initially reacted, and then subsequently the cyanopyridine added (see e.g. Example 16). In other processes, a portion of the aldehyde or ketone has been initially reacted with the electron donor, and then cyanopyridine and additional amounts of the aldehyde or ketone have been added (see e.g. Example 26). In this mode of performing the process, the cyanopyridine and additional aldehyde or ketone can be added together or alternately. By this procedure of initially reacting some or all of the aldehyde or ketone and electron donor prior to the addition of cyanopyridine, preferred yields of carbinol product of at least about 75% have be obtained, and in highly preferred reactions yields of 90% or more have been achieved.

In processes in which the aldehyde or ketone is initially reacted with the electron donor, certain other preferences have also been discovered. In applicants' work, diminished yields have been experienced upon initially reacting ketone and electron donor and then very quickly adding the cyanopyridine. Thus, it is preferred that the initial reacting and the addition of the cyanopyridine be in such a manner as to maximize the yield of desired carbinol product so as to obtain advantageous yields as stated above, which can be facilitated by adding the cyanopyridine gradually rather than all at once or quickly.

On the other hand, advantageously improved yields of about 70% or more can also be obtained where the cyanopyridine, ketone or aldehyde, and electron donor are all added to the solvent prior to bringing the resulting mixture to the reaction temperature.

As to ratios of reactants, the 2- or 4-cyanopyridine is preferably added in slight stoichiometric excess to the ketone or aldehyde, e.g. preferably up to about 10% excess. The electron donor is preferably added in a stoichiometric ratio of about 2:1 or more relative to the ketone or aldehyde.

α-Aryl pyridyl carbinol compounds produced as discussed above can be conventionally hydrogenated using well known techniques to form corresponding α-aryl piperidyl carbinol compounds. However, still another preferred feature of the invention relates to a such a hydrogenation process which is conducted in benzene or an alkylbenzene (i.e. having one or more alkyl groups attached to the benzene ring, e.g. mono-, di- or trialkylbenzenes) solvent, preferably a lower alkylbenzene (e.g. wherein the alkyl group or groups are about $C_1$ to $C_4$ alkyl) such as xylene or toluene solvent. In this regard, it has surprisingly been discovered that the aromatic pyridine ring of these α-aryl pyridyl carbinols, e.g. α-pyridyl diphenyl carbinols, can be successfully hydrogenated essentially without hydrogenation of these aromatic hydrocarbon solvents. Thus, advantageously, the solvent employed in the hydrogenation can be the same as that employed in the preparation of the carbinol as discussed above. Supported palladium catalysts, for example palladium on carbon or other similar catalysts that selectively hydrogenate the pyridyl carbinol, are preferred.

While the invention has been described in detail in the foregoing paragraphs, the same is to be considered as illustrative and not restrictive in character, it being understood that only the preferred embodiments have been described and that all changes and modifications that come within the spirit of the invention are desired to be protected. The following specific Examples are given in further explanation and description of these embodiments, but are intended to be exemplary and not limiting thereof.

EXAMPLE 1

4-Pyridyl Diphenyl Carbinol

To a 500 mL RB flask were charged 4-cyanopyridine (10.4 g, 0.1 mole) and benzophenone (18.2 g, 0.1 mole). To this, xylene (250 mL) and sodium metal (5.0 g, 0.22 mole) cut into small pieces were added. The flask was heated slowly and refluxed under an inert atmosphere (e.g. nitrogen) with magnetic stirring for 3 hours. The color of the reaction mixture changed from clear to dark blue to dark brown during this time. The reaction mixture was cooled to room temperature and water was carefully added (150 mL). The solid product was filtered and washed with water and acetone. 4-pyridyl diphenyl carbinol (18.3 g, 70% yield) was thus recovered with m.p. 238°–240° C.

EXAMPLE 2

4-Pyridyl Diphenyl Carbinol

To a 3-necked 500 mL RB flask fitted with a mechanical stirrer were charged 4-cyanopyridine (10.4 g, 0.1 mole) and benzophenone (18.2 g, 0.1 mole). Dry liquid ammonia was carefully added (250 mL) and the starting materials were dissolved. Sodium metal was then added (5.0 g, 0.22 mole) slowly in small pieces. The reaction mixture was stirred for 1 hour and the ammonia allowed to evaporate. Toluene (150 mL) and water (150 mL) were then added to the residue and the resulting mixture was stirred for 15 minutes. The precipitated product was filtered and washed with water, giving 4-pyridyl diphenyl carbinol.

EXAMPLE 3

4-Pyridyl Diphenyl Carbinol

To a 100 mL RB flask were charged 4-cyanopyridine (0.52 g, 0.005 mole) and benzophenone (0.91 g, 0.005 mole). To this was added THF (25 mL) and the starting materials dissolved. Under an inert atmosphere (nitrogen), samarium diiodide (0.01 mole) in THF (100 mL) was then added. The complete mixture was then stirred at 30° C. for 3 hours. Work up with aqueous $NaHCO_3$ (saturated) gave a solid which was filtered off. The filtrate was extracted with methylene chloride (100 mL) and on evaporation of the methylene chloride gave 4-pyridyl diphenyl carbinol.

EXAMPLES 4–8

Using procedures analogous to Examples 1 and 2 above, 4-pyridyl diphenyl carbinol was produced by reaction of 4-cyanopyridine and benzophenone using varying solvents, conditions and electron donors. The results of Examples 1–3 and this further testing are set forth in Table 1. In Table 1, "ammonia" means liquid ammonia.

TABLE 1

| Ex. | Cyanopyridine | α-aryl carbonyl | Donor | Solv | Temp. | Time | Product |
| --- | --- | --- | --- | --- | --- | --- | --- |
| 1 | 4-cyanopyridine | benzophenone | Na | xylene | reflux | 3 h | 4 pyridyl diphenyl carbinol |
| 2 | 4-cyanopyridine | benzophenone | Na | ammonia | reflux | 2 h | 4-pyridyl diphenyl carbinol |
| 3 | 4-cyanopyridine | benzophenone | $Sm^{2+}$ | THF | 30° C. | 3 h | 4-pyridyl diphenyl carbinol |
| 4 | 4-cyanopyridine | benzophenone | Na | toluene | reflux | 3 h | 4-pyridyl diphenyl carbinol |
| 5a | 4-cyanopyridine | benzophanone | Na | xylene | reflux | 3 h | 4-pyridyl diphenyl carbinol |
| 6b | 4-cyanopyridine | benzophenone | Na | xylene | refluk | 3 h | 4-pyridyl diphenyl carbinol |
| 7 | 4-cyanopyridine | benzophenone | Ca | ammonia | reflux | 3 h | 4-pyridyl diphenyl carbinol |
| 8 | 4-cyanopyridine | benzophanone | Li | ammonia | reflux | 3 h | 4-pyridyl diphenyl carbinol | a benzophenone and Na refluxed for 1 hour and then 4-cyanopyridine added
b 4-cyanopyridine and Na refluxed for 1 hour and then benzophenone added

EXAMPLE 9

2-Pyridyl Diphenyl Carbinol

Example 1 was repeated except 4-cyanopyridine was replaced by 2-cyanopyridine. 2-Pyridyl diphenyl carbinol was produced and recovered in 70% yield.

EXAMPLE 10

4-Pyridyl 4-Methoxyphenyl Phenyl Carbinol

Example 1 was repeated, replacing benzophenone with 4-methoxybenzophenone. 4-Pyridyl 4-methoxyphenyl phenyl carbinol was thereby produced and recovered.

EXAMPLE 11

4-Pyridyl α-Methylstyryl Phenyl Carbinol

Example 1 was repeated, except replacing benzophenone with acetophenone, thus giving 4-pyridyl α-methylstyryl phenyl carbinol as product.

EXAMPLES 12–15

Using procedures analogous to those described above, varying α-aryl carbonyls (i.e. ketones and aldehydes) were reacted with 4-cyanopyridine to give α-4-pyridyl α-aryl carbinol compounds. The results of Examples 9–11 and this further testing are set forth in Table 2. In Table 2, "ammonia" means liquid ammonia.

TABLE 2

| Ex. | Cyanopyridine | α-aryl carbonyl | Donor | Solvent | Temp. | Product |
|---|---|---|---|---|---|---|
| 9 | 2-cyanopyridine | benzophenone | Na | xylene | reflux | 2-pyridyl diphenyl carbinol |
| 10 | 4-cyanopyridine | 4-methoxybenzophenone | Na | xylene | reflux | 4-pyridyl 4-methoxyphenyl phenyl carbinol |
| 11 | 4-cyanopyridine | acetophenone | Na | xylene | reflux | 4-pyridyl α-methylstyryl phenyl carbinol |
| 12 | 4-cyanopyridine | Michler's ketone | Na | xylene | reflux | 4-pyridyl bis-4-(dimethylamino)phenyl carbinol |
| 13 | 4-cyanopyridine | chalcone | Na | xylene | reflux | 4-pyridyl styryl phenyl carbinol |
| 14 | 4-cyanopyridine | benzaldehyde | Na | xylene | reflux | 4-pyridyl phenyl carbinol |
| 15 | 4-cyanopyridine | 4-benzoylpyridine | Na | xylene | reflux | di-4-pyridyl phenyl carbinol |

EXAMPLE 16

4-Pyridyl Diphenyl Carbinol

Benzophenone (54.6 grams, 0.3 mole) was charged into a 1 liter roundbottom three neck flask equipped with a mechanical stirrer, reflux condenser and dropping funnel. Xylene (300 ml) and sodium metal (16.6 grams, 0.72 mole) cut into small pieces were then added. The flask was heated slowly and refluxed under an inert atmosphere (nitrogen) with mechanical stirring for 30 minutes. 4-cyanopyridine (38.2 grams, 0.37 mole) dissolved in xylene (200 ml) was then added over a period of 1 hour, whereafter the mixture was refluxed for an additional three hours. The reaction mixture was then cooled to room temperature and water (300 ml) was carefully added. The solid was then filtered and washed with water and acetone to give 4-pyridyl diphenyl carbinol (73.1 grams, 93% yield)

EXAMPLE 17

4-Pyridyl Diphenyl Carbinol

To a solution of 4-cyanopyridine (5.2 g, 0.05 mole) and benzophenone (9.1 g, 0.05 mole) in iso-propanol was added acetic acid (6.0 g, 0.1 mole) and magnesium metal (1.2 g, 0.05 mole). The resulting mixture was stirred at room temperature for 4 h. The precipitated product was filtered and washed with acetone, and upon analysis found to be 4-pyridyl diphenyl carbinol.

EXAMPLE 18

4-Pyridyl Diphenyl Carbinol

The procedure of Example 17 was repeated, except the solvent was changed from i-propanol/acetic acid to toluene/aqueous ammonium chloride (2 equivalents of solid in water). GC of the organic layer showed the formation of the product, 4-pyridyl diphenyl carbinol.

EXAMPLE 19

4-Pyridyl Diphenyl Carbinol

The procedure of Example 17 was repeated, except replacing magnesium with zinc. The recovered product was identified as 4-Pyridyl diphenyl carbinol.

EXAMPLE 20

4-Pyridyl Diphenyl Carbinol

The procedure of Example 18 was repeated, except replacing magnesium with zinc and using MeOH/aqueous ammonium chloride as the solvent. 4-pyridyl diphenyl carbinol was recovered as product.

EXAMPLE 21

4-Pyridyl Diphenyl Carbinol

A mixture of 4-cyanopyridine (5.2 g, 0.05 mole), benzophenone (9.1 g, 0.05 mole) and zinc (3.3 g, 0.05 mole) was refluxed in acetic anhydride (200 mL) under nitrogen for 3 h. The acetic anhydride layer on analysis by GC showed 4-pyridyl diphenyl carbinol product.

EXAMPLE 22

4-Pyridyl Diphenyl Carbinol

The procedure of Example 17 was repeated except here acetic acid was replaced with aqueous acetic acid and the metal magnesium was replaced with aluminum. The mixture was refluxed for 5 h, cooled and neutralized with base to give the product 4-pyridyl diphenyl carbinol.

EXAMPLE 23

4-Pyridyl Diphenyl Carbinol

The reaction was conducted as in Example 22 except the solvent was MeOH/aqueous acetic acid and the metal was tin. The mixture was refluxed for 4 h, cooled and neutralized with base. Extraction of the mixture with xylene followed by GC analysis showed the product, 4-pyridyl diphenyl carbinol in the xylene layer.

EXAMPLE 24

4-Pyridyl Diphenyl Carbinol

A mixture of 4-cyanopyridine (2.6 g, 0.025 mole), benzophenone (4.6 g, 0.025 mole) and chromium metal powder (1.3 g, 0.025 mole) was stirred in MeOH (100 mL). To this mixture was added aqueous hydrochloric acid (3 equivalents) and the mixture stirred for 3 h at room temperature.

Analysis of the MeOH solution showed 4-pyridyl diphenyl carbinol as product.

EXAMPLE 25

4-Pyridyl Diphenyl Carbinol

The procedure of Example 24 was repeated except manganese metal was used instead of chromium. Again, GC analysis showed the 4-pyridyl diphenyl carbinol product.

EXAMPLE 26

4-Pyridyl Diphenyl Carbinol

Sodium (16.6 grams, 0.72 mole) metal and xylene (150 ml) were charged into a 1 liter round bottom three-neck flask equipped with a mechanical stirrer, reflux condenser and two dropping funnels. The mixture was brought to reflux and the addition of benzophenone (54.6 grams, 0.3 mole) was begun. When about ¼ to ⅓ of the benzophenone had added during 15–30 minutes, the addition of a solution of 4-cyanopyridine (38.2 grams, 0.37 mole) in xylene (200 mL) was begun at a rate so that about ½ of the cyanopyridine solution had been added when the addition of benzophenone was complete. The remaining cyanopyridine solution was added during another 30 minutes. Upon work-up with water (300 mL), 4-pyridyl diphenyl carbinol was obtained in about 95% yield.

EXAMPLE 27

Diphenyl 4-Piperidyl Carbinol (Azacyclonol)

A 1.4 liter hydrogenation shaker bomb was charged with 4-pyridyl diphenyl carbinol (46.5 grams, 0.18 mole), platinum oxide (2.0 grams) and glacial acetic acid (325 ml). The bomb was sealed, pressurized with hydrogen to 200 psi, and heated with shaking to 75° C. for 3 hours. The bomb was then cooled and the contents filtered and evaporated to remove the acetic acid. After evaporation, the material was neutralized with aqueous sodium hydroxide (120 grams of 50% NaOH and 330 ml water). The solid material was thereafter filtered and washed with cold water to give on drying diphenyl 4-piperidyl carbinol (Azacyclonol) (43.2 grams, 91% yield). To an ethanolic solution of Azacyclonol was added hydrogen chloride, thus giving Azacyclonol hydrochloride salt.

EXAMPLE 28

Diphenyl 4-Piperidyl Carbinol

A 1.4 L hydrogenation shaker bomb was charged with 43.00 grams (0.165 moles) diphenyl-4-pyridylcarbinol, 8.00 grams 50% $H_2O$ wet 5% Pd on carbon (4 grams dry) and 350 ml xylene. The bomb was sealed, pressurized with 900 psi $H_2$, and heated with shaking to 170° C. After 17 hours, the pressure was 1075 psi (at 170° C.) and the bomb was allowed to cool. The contents are poured out, heated to 70° C. and suction filtered carefully to remove the catalyst. GC analysis of the filtrate and washes at this point indicated 6.9% azacyclonol and 0.05% diphenyl-4-pyridylcarbinol. The filtrate was topped off on a rotary evaporator to a constant weight (42.65 grams). The sticky crude azacyclonol was removed and recrystallized from 200 ml heptane and 165 ml xylene. After chilling, filtration and over drying (2 hours, 100° C., 15 mm) a yield of 37.84 grams or 86.0% of azacyclonol was obtained, having a melting point of 163°–166° C.

What is claimed is:

1. A process for producing an α-2-pyridyl α-aryl carbinol or an α-4-pyridyl α-aryl carbinol compound, comprising reacting a 2- or 4-cyanopyridine with an α-aryl ketone or aldehyde in the presence of a metal or metal ion electron donor and recovering therefrom the α-2-pyridyl α-aryl carbinol or α-4-pyridyl α-aryl carbinol compound;

wherein the aryl group of said reactant and the produced compound has up to 14 carbon atoms and up to three fused rings.

2. The process of claim 1, comprising
   initially reacting α-aryl aldehyde or ketone in the presence of the metal or metal ion electron donor;
   subsequently reacting the product of said initial reacting with the 2- or 4-cyanopyridine; and
   recovering therefrom the α-2-pyridyl α-aryl carbinol or α-4-pyridyl α-aryl carbinol compound.

3. The process of claim 1, comprising:
   heating and reacting the α-aryl aldehyde or ketone with the 2- or 4-cyanopyridine in the presence of the metal or metal ion electron donor in an aromatic solvent; and
   recovering therefrom the α-aryl pyridyl carbinol compound.

4. The process according to claims 1, 2, or 3 wherein said reacting includes reacting an α-aryl ketone.

5. The process any of claims 1–3 wherein said reacting includes reacting an α-aryl aldehyde.

6. The process of claim 4 wherein said reacting includes reacting an α,α-diaryl ketone.

7. The process of claim 6 wherein the electron donor is a Group IA or IIA metal.

8. The process of claim 6 wherein the α,α-diaryl ketone is an α,α-diphenyl ketone.

9. The process of claim 8 wherein said α,α-diphenyl ketone is benzophenone.

10. The process of claim 8 wherein the electron donor is a Group IA or IIA metal.

11. The process of claim 10 wherein the electron donor is sodium metal or lithium metal.

12. The process of claim 11 wherein the electron donor is sodium metal.

13. The process of claim 9 wherein the electron donor is a Group IA or IIA metal.

14. The process of claim 13 wherein the electron donor is sodium metal or lithium metal.

15. The process of claim 14 wherein the electron donor is sodium metal.

16. The process of claim 14 wherein said cyanopyridine is a 2-cyanopyridine.

17. The process of claim 15 wherein said cyanopyridine is a 2-cyanopyridine.

18. The process of claim 17 wherein said cyanopyridine is 2-cyanopyridine and which includes recovering 2-pyridyl diphenyl carbinol as product.

19. The process of claim 14 wherein said cyanopyridine is a 4-cyanopyridine.

20. The process of claim 15 wherein said cyanopyridine is a 4-cyanopyridine.

21. The process of claim 20 wherein said cyanopyridine is 4-cyanopyridine and which includes recovering 4-pyridyl diphenyl carbinol as product.

22. The process of claim 2 wherein said initial reacting and said subsequent reacting are conducted with heating in an aromatic solvent.

23. The process of claim 22 wherein the solvent is an aromatic hydrocarbon solvent and wherein said recovering includes hydrolyzing a corresponding carbinol salt to produce the carbinol.

24. The process of claim 23 which includes initially reacting a portion of the total amount of α-aryl ketone or aldehyde to be reacted, and thereafter charging the 2- or 4-cyanopyridine and additional of the ketone or aldehyde to the reaction mixture.

25. The process of claim 24 which includes reacting benzophenone with 2- or 4-cyanopyridine to form 2- or 4-pyridyl diphenyl carbinol.

26. The process of claim 25 wherein the reacting is at reflux.

27. The process of claim 26 wherein the total amount of benzophenone to be reacted is charged prior to completing the charge of 2- or 4-cyanopyridine.

28. The process of claim 27 wherein the cyanopyridine is 4-cyanopyridine and which includes recovering 4-pyridyl diphenyl carbinol as product.

* * * * *

UNITED STATES PATENT AND TRADEMARK OFFICE
CERTIFICATE OF CORRECTION

PATENT NO : 5,541,331

DATED : July 30, 1996

INVENTOR(S): Ramiah Murugan et al.

It is certified that error appears in the above-identified patent and that said Letters Patent is hereby corrected as shown below:

In col. 1, line 26, please delete "feradine" and insert in lieu thereof --fenadine--.

In col. 1, line 31, please delete "puridyl" and insert in lieu thereof --pyridyl--.

In col. 1, line 38, please delete "the".

In col. 1, line 46, please add --n-- to "Tetrahedro".

In col. 1, line 48, please delete "Tshitschibabin" and insert in lieu thereof --Tschitschibabin--.

In col. 1, line 51, please delete "Nagarjan" and insert in lieu thereof --Nagarajan--.

In col. 1, line 51, please delete "H." and insert in lieu thereof --K.--.

In col. 1, line 56, please delete "puridinium" and insert in lieu thereof --pyridinium--.

In col. 2, line 3, please delete "DMOS" and insert in lieu thereof --DMSO--.

In col. 2, line 15, please delete "organmetallics" and insert in lieu thereof --organometallics--.

In col. 2, line 33, please add --s-- after "need".

In col. 2, line 59, please delete "puridyl" and insert in lieu thereof --pyridyl--.

In col. 2, line 64, please add --d-- after "feature".

In col. 3, line 33, please add --s-- after "purpose".

In col. 3, line 33, please delete "and" and insert in lieu thereof --an--.

In col. 3, line 50, please add --d-- after "desire".

In col. 4, line 3, please delete "data" and insert in lieu thereof --date--.

UNITED STATES PATENT AND TRADEMARK OFFICE
CERTIFICATE OF CORRECTION

PATENT NO : 5,541,331
DATED : July 30, 1996
INVENTOR(S): Ramiah Murugan et al.

It is certified that error appears in the above-identified patent and that said Letters Patent is hereby corrected as shown below:

In col. 4, line 30, please delete "s" after "ketone".

In col. 4, line 43, please delete "above Py," and insert in lieu thereof --above, Py--.

In col. 4, line 61, please delete "One Other" and insert in lieu thereof --On the--.

In col. 5, line 55, please delete "data" and insert in lieu thereof --date--.

In col. 5, line 64, please delete "data" and insert in lieu thereof --date--.

In col. 6, line 5, please delete "are" and insert in lieu thereof --as--.

In columns 7 and 8, Table 1, in Ex. 5a (col. 2), please delete "benzophanone" and insert in lieu thereof --benzophenone--.

In columns 7 and 8, Table 1, in Ex. 8 (col. 2), please delete "benzophanone" and insert in lieu thereof --benzophenone--.

In col. 11, line 20, please add --been-- in between "had" and "added".

In col. 11, line 66, please delete "over" and insert in lieu thereof --oven--.

In col. 12, line 29 (claim 5), please delete "any of claims 1-3" and insert in lieu thereof --according to claims 1, 2 or 3--.

Signed and Sealed this

Eleventh Day of August 1998

*Attest:*

BRUCE LEHMAN

*Attesting Officer*  *Commissioner of Patents and Trademarks*